United States Patent [19]
Chan

[11] Patent Number: 5,958,300
[45] Date of Patent: Sep. 28, 1999

[54] COMPOSITION FOR PATIENT SAMPLE PREPARATION

[75] Inventor: Raymond Chan, Redwood City, Calif.

[73] Assignee: Genzyme Corporation, Framingham, Mass.

[21] Appl. No.: 09/019,831

[22] Filed: Feb. 6, 1998

[51] Int. Cl.[6] .................................................. G01N 31/00
[52] U.S. Cl. ........................ 252/408.1; 436/18; 436/176
[58] Field of Search ........................... 252/408.1; 436/18, 436/174, 176

[56] References Cited

U.S. PATENT DOCUMENTS

| | | | |
|---|---|---|---|
| 4,260,599 | 4/1981 | Okazaki et al. | 424/122 |
| 4,948,726 | 8/1990 | Longoria | 435/7 |
| 5,164,485 | 11/1992 | Yukio et al. | 530/350 |
| 5,212,297 | 5/1993 | Colella et al. | 536/24.31 |
| 5,328,913 | 7/1994 | Murad et al. | 514/275 |
| 5,593,859 | 1/1997 | Prockop et al. | 435/69.1 |

FOREIGN PATENT DOCUMENTS

| | | | |
|---|---|---|---|
| 92/08971 | 5/1992 | WIPO | 436/18 |

*Primary Examiner*—William H. Beisner
*Attorney, Agent, or Firm*—F. Brad Salcedo

[57] ABSTRACT

The object of the present invention is to claim a composition which when added to a patient sample containing a target antigen in an acidic or formalin-containing transport medium neutralizes the acid and formalin while preserving immunoreactivity of the antigen allowing its detection. The composition comprises an amino glycol buffer, an amino acid, a salt, and a non-ionic detergent. A further object of the present invention is to claim a method of processing a sample by adding a composition comprising an amino glycol buffer, an amino acid, a salt, and a non-ionic detergent.

5 Claims, No Drawings

COMPOSITION FOR PATIENT SAMPLE PREPARATION

BACKGROUND OF THE INVENTION

Enteric stool specimens are frequently collected in a 10% formalin or sodium acetate-acetic acid-formalin (SAF) transport medium which serves to inactivate the infectivity and preserve the morphology of parasitic organisms in the sample. These media may have adverse effects on the function of antibodies in diagnostic immunoassays.

Formalin, also known as formaldehyde, binds to amino groups on proteins, potentially altering their structure and functional activity. Low pH, such as from the acetic acid in SAF, is inhibitory to antigen-antibody binding.

The development of an effective diagnostic immunoassay for enteric stool specimens collected in formalin or SAF, therefore, depends on the ability to counteract these adverse effects. Although some microwell and flow-through enzyme immunoassays appear to accomplish this through sample dilution, simpler and more effective approaches are needed.

SUMMARY OF THE INVENTION

The object of the present invention is to claim a composition which when added to a patient sample containing a target antigen in an acidic or formalin-containing transport medium neutralizes the acid and formalin while preserving immunoreactivity of the antigen allowing its detection. The composition comprises an amino glycol buffer, an amino acid, a salt, and a non-ionic detergent.

A further object of the present invention is to claim a method of processing a sample by adding a composition comprising an amino glycol buffer, an amino acid, a salt, and a non-ionic detergent.

DETAILED DESCRIPTION OF THE INVENTION

The present invention is based on the discovery that a composition comprising an amino glycol buffer, an amino acid, a salt, and a non-ionic detergent can, when added to a patient sample containing a target antigen in an acidic or formalin-containing transport medium, allow for the neutralization of the acid and formalin while preserving immunoreactivity of the antigen allowing its detection.

The composition of the present invention includes an amino glycol buffer. Suitable amino gylcol buffers include 2-amino-2hydroxymethyl-1,3-propanediol (Tris buffer), 2-amino-2-methyl-1,3-propanediol.

The present composition further includes an amino acid. Suitable amino acids include glycine, lysine and arginine.

The composition further includes a salt. Suitable salts include sodium salts such as sodium chloride and potassium salts such as potassium chloride.

The composition of the present invention further includes a non-ionic detergent. Suitable non-ionic detergents include polyoxyethylenes such as t-octylphenoxypolyethoxyethanol (Triton X-100) and (octylphenoxyl)-polyethoxyethanol (Nonidet P-40).

The composition of the present invention may further include serum. It is believed that serum serves to prevent or reduce non-specific binding of antibodies that may be subsequently used in an immunoassay when non-specific binding is a problem. Suitable serums include normal mammalian serum of any kind, such as that derived from humans. Other mammalian serums include bovine, porcine, equine and murine.

Formulation

The key elements of the treatment buffer formulation are the use of an amino acid in a basic buffer medium. We have selected glycine as the amino acid, and Tris base as the basic buffer. Also included in the treatment buffer is some detergent, Triton X-100, which appears to help extract antigens relevant to our specific assay from the stool matrix, sodium chloride to help mimic physiological salt conditions which are theoretically ideal for antigen-antibody binding to occur, and sodium azide, which is added as an anti-microbial preservative. In addition, normal bovine serum was added to block non-specific binding.

The final formulation consists of 1 M Tris, 1 M glycine, 0.9% sodium chloride, 0.5% Triton X-100, and 0.01% sodium azide. The sources of the chemicals we have used to develop the treatment buffer are the Sigma Chemical Company (St. Louis, Mo. USA) and the J.T. Baker Chemical Company (Phillipsburg, N.J. USA). The vendor catalog numbers are: Tris Base (also known as Trizma Base), Sigma T-1503; Glycine, Sigma G-7126; Sodium chloride, Baker 3624-07; Triton X-100, Sigma T-6878; and Sodium azide, Sigma S-2002. These chemicals are standard grade materials and we have no reason to believe that other sources of these chemicals would not be equally as effective.

Efficacy

The need for a treatment buffer became apparent during our early development work on lateral flow immunoassays where a stool specimens was the patient sample being tested. It was noted that 10% formalin or SAF when run directly in our lateral flow assays severely weakened or completely eliminated the development of test and control lines.

Therefore, tests were run in an attempt to eliminate the interference caused by formalin using a Group A Streptococcus assay (Rapid Strep A test, Genzyme Diagnostics, San Carlos, Calif.) and an Infectious Mononucleosis assay (Rapid Mono test, Genzyme Diagnostics), both lateral flow assays. We discovered that formalin or SAF did not cause an antibody-specific inhibition of signal, but was a more generalized phenomenon that would be applicable to many different immunoassays of this type.

Initially, after demonstrating that adding various types of carrier proteins was relatively ineffective in counteracting formalin, glycine was tried and shown to be effective. However when SAF-treated stool samples were tested, significant inhibitory effects on signal were still observed. It appears that this inhibition was caused by the presence of acetic acid, which made the samples rather acidic in pH. When Tris base was added to such samples, signal was restored.

The data shown in the table below illustrates the suppressive effects of SAF on control line signal development in a lateral flow assay. These assays utilize goat anti-mouse IgG antibody striped onto a membrane, which in turn captures a particulate-labeled mouse IgG antibody to generate a visible signal. As shown, the use of the sample treatment buffer (STB) restores the control line signal to approximately the same intensity as the control level.

TABLE

| Sample | Device Control Line Intensity |
| --- | --- |
| Control (water) | ++++ |
| Without STB (SAF + water) | − |
| With STB (SAF + STB | ++++ |

In the above experiments, no formal incubation time was used. The treatment buffer was added immediately prior to pipeting the sample into the test devices. The chemical reactions, which neutralize formalin and acid occur quickly and functionally, can be thought of as instantaneous. It is possible that additional neutralization may take place as the sample is flowing in the device.

Equivalents

Those skilled in the art will recognize, or be able to ascertain, using no more than routine experimentation, many equivalents to the specific embodiments of the invention described herein. Such equivalents are intended to be encompassed by the following claims:

The invention claimed is:

1. A composition comprising an amino glycol buffer, an amino acid, a salt and a non-ionic detergent, wherein the concentration of the amino glycol buffer is about 1M.

2. The composition of claim 1, wherein the amino glycol is selected from the group consisting of 2-amino-2hydroxymethyl-1,3-propanediol, 2-amino-2-methyl-1,3-propanediol, and mixtures thereof.

3. The composition of claim 1, wherein the amino acid is selected from the group consisting of glycine, lysine, arginine, and mixtures thereof.

4. The composition of claim 1, wherein the salt is selected from the group consisting of sodium salt, potassium salt, and mixtures thereof.

5. The composition of claim 1, wherein the non-ionic detergent is selected from the group consisting of t-octylphenoxypolyethoxyethanol (Triton X-100) (octylphenoxyl)-polyethoxyethanol (Nonidet P-40), and mixtures thereof.

* * * * *